United States Patent

Somers et al.

[11] Patent Number: 4,632,100
[45] Date of Patent: Dec. 30, 1986

[54] SUTURE ANCHOR ASSEMBLY

[75] Inventors: W. Karl Somers; Marlowe E. Goble, both of Logan, Utah

[73] Assignee: Marlowe E. Goble, Cache County, Utah

[21] Appl. No.: 770,428

[22] Filed: Aug. 29, 1985

[51] Int. Cl.$^4$ .............................................. A61F 5/04
[52] U.S. Cl. ..................................... 128/92; 128/330; 128/92 E; 623/13
[58] Field of Search ............... 128/303 R, 303 B, 330, 128/92 R, 92 EB, 92 E, 92 A, 335.5; 623/13

[56] References Cited

U.S. PATENT DOCUMENTS

| | | | |
|---|---|---|---|
| 3,003,155 | 10/1961 | Mielzynski et al. | 128/330 |
| 3,699,969 | 10/1972 | Allen | 128/330 |
| 3,862,453 | 1/1975 | Widdifield | 128/330 |
| 3,953,896 | 5/1976 | Treace | 623/13 |
| 3,988,783 | 11/1976 | Treace | 623/13 |
| 4,175,555 | 11/1979 | Herbert | 128/92 B |
| 4,289,124 | 9/1981 | Zickel | 128/92 B |
| 4,301,551 | 11/1981 | Dore et al. | 623/13 |
| 4,400,833 | 8/1983 | Kurland | 623/13 |
| 4,414,967 | 11/1983 | Shapiro | 128/92 B |
| 4,537,185 | 8/1985 | Stednitz | 128/92 B |

Primary Examiner—Gene Mancene
Assistant Examiner—C. W. Shedd
Attorney, Agent, or Firm—M. Reid Russell

[57] ABSTRACT

A cylindrical suture anchor having a drill formed on one end thereof and flights of threads formed on the other whereto at least one section of suture is permanently secured, the anchor to be turned through a driver maintained and turned by a separate drilling device operated by an orthopedic surgeon. In practice, the surgeon positions the suture anchor drill end on a point on a bone mass in a human body and, by turning the driver, turns the suture anchor to drill into the bone mass, until a first thread flight engages the drilled hole wall and is turned therein, tapping that hole, to receive each following thread flight, until the anchor is seated therein, during which seating the driver is telescoped out of a splined coupling to the anchor and a suture secured in a longtudinal opening in the anchor that is folded into the driver is pulled from that driver for use by the orthopedic surgeon in securing a ligament to that point on the bone mass.

15 Claims, 7 Drawing Figures

SUTURE ANCHOR ASSEMBLY

FIELD OF THE INVENTION

This invention relates generally to appliances for use during certain orthopedic surgical procedures to anchor a suture to a bone mass whereafter that suture can be used to attach and maintain a ligament to that bone mass.

PRIOR ART

It has long been a problem to anchor a suture to a bone mass for applying or otherwise securing with that suture a ligament to that bone mass to hold that ligament against that bone mass so that it will attach thereto during the body's healing process. Such anchoring is particularly difficult in a tight space or confined area as may be all that is available to a surgeon and has formerly involved the separate steps of: drilling a hole in the bone mass; turning a device therein such as one that incorporates an eyelet; and thereafter threading a suture through that eyelet. Such procedure, particularly in a tight or confined area that a surgeon often must operate within, is difficult and with the number of steps involved is obviously very time consuming. Additionally, in the process of performing the steps of drilling and tapping a hole, it is not uncommon for a surgeon to have to drill a number of holes before one is produced that will properly receive an anchor turned therein.

Heretofore, a number of arrangements have been employed for securing a suture to a body part. One such arrangement is shown in a patent by Furlow et al., U.S. Pat. No. 4,244,370 that is a device of positioning an implant within body soft tissue and is not concerned with anchoring to a bone mass as is the present invention. Where devices have been employed for assisting in the insertion of surgical appliances into bone tissue, such have been like that shown in a patent by Asnis, et al., U.S. Pat. No. 4,383,527 that is a device for use with a conventional drill to position guide pins for drilling into a bone mass. Devices for installing rods or pins into bone tissue, like that set out in the above cited Asnis, et al. patent, are, of course, well known and do not anticipate the present invention in either structure or function.

Examples of tools for practicing orthopedic procedures are shown in patents by Morrill, U.S. Pat. No. 4,140,111 and by Troutner, et al, U.S. Pat. No. 4,091,880, that are drill arrangements and can be used with the present invention. Additionally, a drill arrangement for forming a cavity within a bone mass is shown in a patent by Raftopoulos, et al., U.S. Pat. No. 4,337,773, that, while it does involve a device for drilling into a bone mass, is structurally and functionally unlike the present invention.

Heretofore, installation or mounting of a suture anchor to a bone, as set out above, has generally been a multistep process and has often been accomplished under very difficult conditions as when a surgeon has to operate in a confined area within a human body. Such accessability considerations have often limited the ability of the surgeon to secure sutures at locations on a bone mass he deems to be most desirable, forcing that surgeon to settle for a location that is more accessible. The present invention, by providing a device for use in a single operational step that is suited for use in a very narrow or confined area, allows the surgeon to implant an anchor with a preattached suture secured thereto at an optimum bone mass location as he selects to fix a ligament thereto. The present invention, therefore, functions to facilitate the process of anchoring a suture to a bone mass. Further, because such suture can be exactly placed at a most desirable bone mass location, its use improves the results that can be expected to be obtained from a surgical procedure wherein it is used.

SUMMARY OF THE INVENTION

It is therefore, a general object of the present invention to provide a suture anchor and driver therefore for use in a surgical procedure where a suture is to be secured to a bone mass to receive a ligament secured thereto.

Another object of the present invention is to provide a suture anchor and driver therefore for use in practicing an orthopedic surgical procedure where, with turning the driver, the suture anchor will drill a hole in and be turned into that hole in that bone mass, and with the removal of that driver from engagement with the anchor, a suture secured to that anchor is exposed that extends therefrom and is for attachment to a ligament, or the like, to be used to draw and secure that ligament into healing engagement with that bone mass.

Another object of the present invention is to provide a suture anchor that, in one operation, can be both drilled and turned into a bone mass and includes a suture attached thereto.

Another object of the present invention is to provide a suture anchor that can be easily and efficiently installed into a location on a bone mass even where access to that bone mass location is very limited.

Still another object of the present invention is to provide a suture anchor and driver therefore whereby, with turning of the driver, the suture anchor will drill and be turned into a bone mass so as to be positioned well into the bone mass, which driver includes an arrangement for disengaging from that suture anchor after that suture anchor is seated in said bone mass.

In accordance with the above objects, the present invention in a suture anchor and driver therefore involves a suture anchor that is formed as a single unit to have a double fluted drill formed on one end thereof with flights of locking threads formed distal therefrom on the anchor other end. The threads are formed in flights that slope away from the drill end for turning into a hole formed by the drill into the bone mass when that anchor is turned. The suture anchor includes a longitudinal hole or opening formed therein adjacent the threaded end, which hole is stepped from a greater diameter at an open end adjacent to the threads to a lesser diameter centrally, the opening terminating within the anchor. The lesser diameter portion of the longitudinal hole is to receive a suture retaining disc press fitted into that opening using preferably a disc inserting tool that is arranged to limit disc travel into that longitudinal hole precluding the disc contacting the end thereof to lock therein. The disc receives a suture threaded through a central longitudinal opening thereof and is knotted behind that hole. The knot integrity is protected by a limited entry of the disc into the longitudinal hole through a use of an inserting tool, that tool precluding the suture knot contacting the closed end. The suture retaining disc slopes outwardly from a lesser diameter end to a greater diameter end, and the lesser diameter end is rounded to be fitted first into the anchor longitudinal hole, the suture knotted across that disc lesser diameter end. The suture retaining disc is slid into the anchor longitudinal hole, past the greater diameter portion and into that lesser diameter portion until the disc greater diameter end lodges therein to bind and lock against the opening wall. The suture is thereby secured in to extend rearwardly from that anchor and is, in turn, threaded into the driver.

The larger diameter portion of the anchor longitudinal hole adjacent to the anchor end is faced, preferably, with six equal surfaces therearound to have a hexagonal appearance and is to receive an end of the driver that is likewise shaped to have a hexagonal appearance around the end thereof for closely fitting in that anchor end. Thereby the anchor is mounted to the driver, and the turning of the driver will turn also the anchor.

The driver is formed to include a narrow neck on one end thereof that has the hexagonal shape and, progressing therealong, is stepped outwardly at a right angle to have approximately the anchor drill portion diameter allowing it to follow the anchor into the drilled hole containing along the driver, the driver is again stepped outwardly at a right angle to form a shoulder that is such that, when the suture anchor is turned into the bone mass, the shoulder will butt against the area surrounding that hole. Whereafter, with continued driver turning, that anchor will be turned off of the driver hexagonal end leaving the anchor appropriately seated in that bone mass.

The driver includes a longitudinal hole formed therethrough, which hole is enlarged from a line through the driver to the shoulder rearwardly to accommodate the suture material folded therein. So arranged, as the anchor is turned off the driver, and the driver removed, the suture material will be drawn out of the driver hexagonal end for use in a surgical procedure for joining a ligament to that bone mass. The driver, larger portion, it should be understood, is of sufficient outside diameter to fit into a conventional chuck of a manual or electric motor driven drill that is suitable for use in performing an orthopedic surgical procedure. The combination of the suture anchor and driver is of such diameter as to facilitate their being fitted into a very close or narrow area in a body cavity to allow the surgeon to operate on a point or section of a bone mass that might otherwise have been unavailable or at least very difficult to secure a suture to.

In practice, the suture anchor fitted with the driver is supplied as a unit to an orthopedic surgeon in a sterile state for use in an orthopedic surgical procedure for joining a ligament to a point on a bone mass. In the performance of such surgical procedure, the suture anchor is positioned in a body opening against a bone mass and a chuck holding the driver is turned such that the flute drill end of the anchor will bore a hole into the bone mass, that drill turning therein until a first screw thread flight of the anchor comes into engagement with the side of that hole. That first screw flight will catch in that hole wall and whereafter, with continued turning of the suture anchor, sequential thread flights will be drawn and turned into that bone mass hole as the drill bit continues to bore therein. The suture anchor is turned into that bone mass until a depth is reached whereat a shoulder portion of the driver comes in contact with the outer lip of that hole. The driver is thereby restricted from passing further into that drilled hole, and with continued driver and anchor turning, the anchor will be turned off of the driver end seating the anchor in the bone mass. The driver can thereafter be removed from the body cavity during which removal the suture connected to the anchor is pulled from the driver interior leaving it connected to the anchor embedded in the bone mass. The suture is then available for use by the surgeon to attach a ligament to that bone mass. The suture anchor will remain within the bone mass and the suture material will eventually be absorbed by the body in the healing processes where the ligament grows to that bone mass.

IN THE DRAWINGS

In the drawings is shown that which is presently regarded as the best mode for carrying out the invention;

Figure 5A:
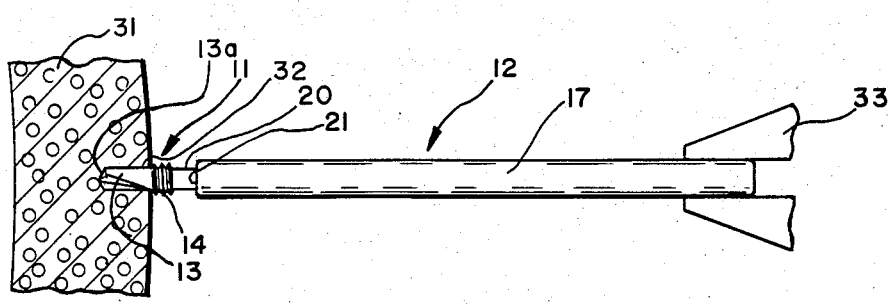
FIG. 5A, shows the suture anchor and driver connected together, the driver end shown maintained in a chuck for turning, the suture anchor drilling into a bone mass.
Figure 5B:
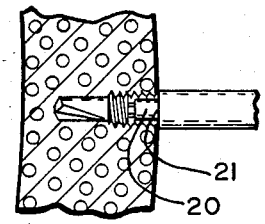
Figure 5C:
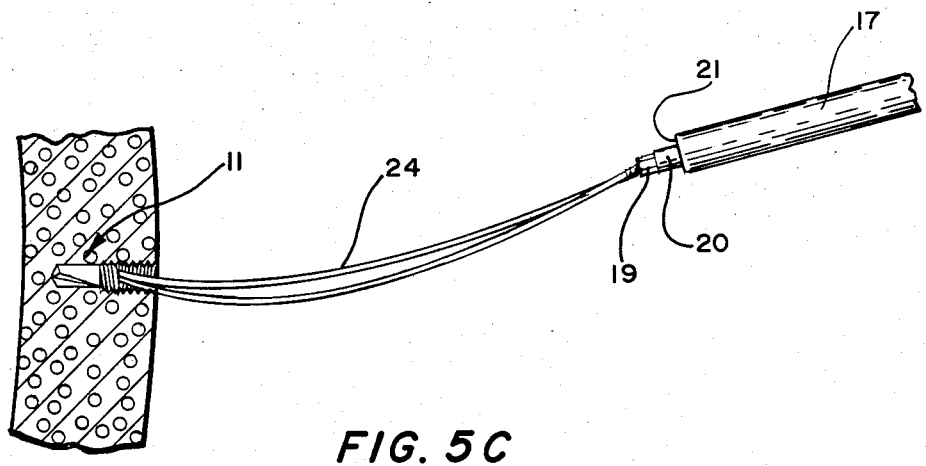

FIG. 5B, shows the suture anchor of FIG. 5A drilling into the bone mass, with flights of threads of that anchor turned into that bone mass to a point where a shoulder of the driver engages the bone mass around the drilled hole; and FIG. 5C, shows the suture anchor seated in a bone mass after the driver has been disconnected therefrom, the suture secured to the suture anchor shown pulling out of that driver end.

DETAILED DESCRIPTION

Orthopedic surgical procedures involving repair of damaged or torn ligaments often includes a requirement that a ligament end be secured to a bone mass by a suture or like arrangement. In such procedure, after the ligament has grown to the bone mass, the suture will be absorbed by the body during that healing process. Obviously, to fix or secure such suture to a bone mass has required some physical connection therebetween. Heretofore, such attachment of a suture to a bone mass has generally involved separate steps of drilling an appropriate hole therein, turning a screwlike device into that hole, and has included some arrangement for attaching a suture to that screwlike device. Such prior procedures have necessitated the surgeon having sufficient room or manual access to a contact point on the bone mass for him to manipulate tools to secure an anchor and fit a suture thereto. Obviously, such need for an open work area has restricted the usability of certain bone mass locations that would perhaps be more desirable for ligament connection in a surgical procedure, necessitating that the surgeon select less desirable locations where he has better access. Therefore, prior to the present invention, it has often been the case that a surgeon practicing a reconstructive surgical procedure for attaching a ligament to a point on a bone mass has encountered circumstances that have dictated that he use a less desirable but more accessible bone area.

Figure 1:
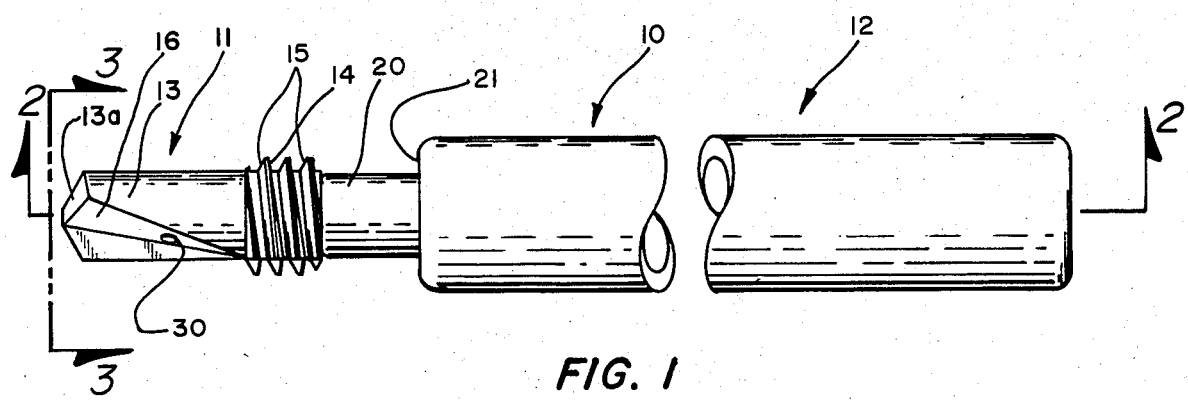
FIG. 1, is a side elevation view of a suture anchor and driver therefore of the present invention.
Figure 2:
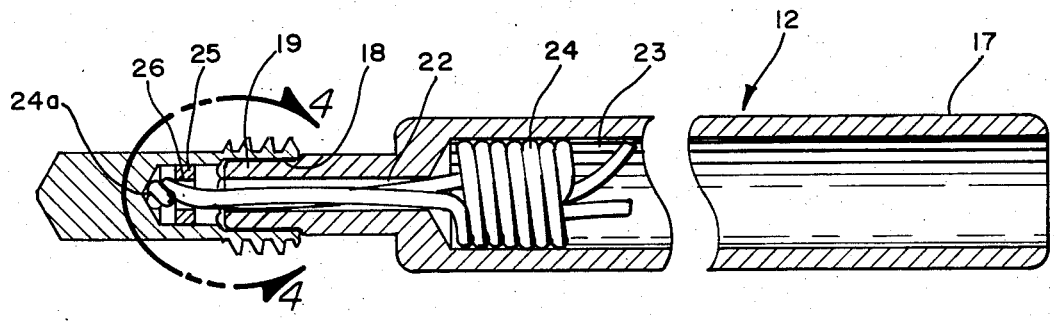
FIG. 2, is a profile sectional view taken along the line 2—2 of FIG. 1 showing the longitudinal interiors of the suture anchor and connected driver of FIG. 1.

FIG. 1 shows the present invention in a suture anchor and driver 10, hereinafter referred to as tool 10, as consisting of an anchor 11 and driver 12 therefore. The one anchor end includes a fluted drill formed thereon that includes a pointed end 13a for contacting a point on a section of bone mass that a surgeon believes will be an optimum point for attaching a ligament to in a practice of a surgical procedure involving reattachment of a ligament to a bone. Thereafter, the surgeon, by turning an end 17 of driver 12, either with a brace or a motor driver chuck arrangement, wherein the driver body 17 is maintained, causes the anchor fluted drill 13 to drill or bore into the bone mass. During which drilling, when the entire length of the fluted drill end 13 has passed into the bone mass, a first flight 15 of threads 14, that are formed on the opposite or distal end of anchor 11 to the fluted drill 13, will engage the lip of the hole bored into the bone mass. Thereafter, with continued driver turning, the threads 14 will be screwed or turned into that bored hole. Continued driver turning therefor moves the anchor threads 14 completely into the bored hole, which anchor is followed therein by a driver collar 20 portion, that collar passing also into the bored hole until a shoulder 21 of driver 12 that is distal from collar 20 and is stepped outwardly at a normal angle therefrom, engages the area of the bone mass around that bored hole. Whereafter, with continued turning, the anchor 11 will turn further into the bone mass until a hexagonal end 19 of the driver 12, as shown best in FIG. 2, is telescoped out of engagement with a hexagonal faced end 18, of the anchor 11. The driver 12 is thereby disengaged from the anchor and can be removed leaving a suture 24 connected within anchor 11 extending therefrom. The surgeon will sense or feel when driver separation occurs and will then cease turning the driver. The anchor 11 is thereby optimumly positioned within the bone mass. Whereafter, the surgeon can connect that suture 24 to a ligament and draw and secure that ligament into healing engagement with the bone mass surface, completing the procedure.

Figure 4:
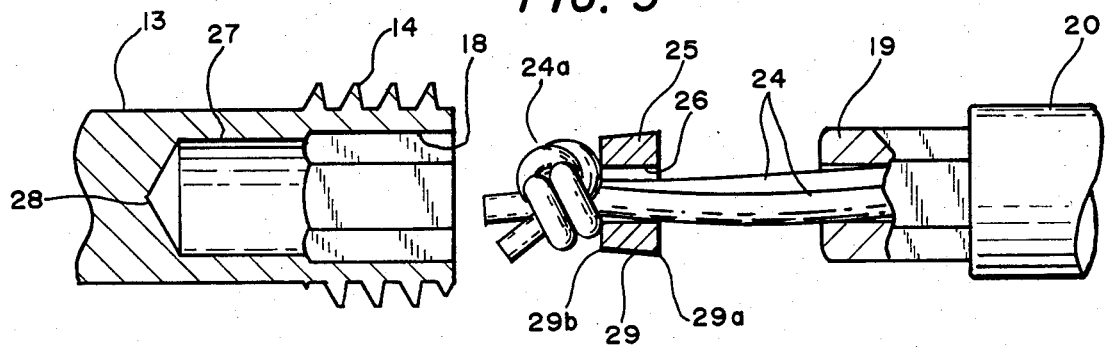
FIG. 4, is an expanding exploded sectional view taken within the line 4—4 of FIG. 2 showing a suture retaining disc with a suture knotted across one face aligned for installation in the longitudinal opening in the suture anchor and showing a hexagonal sided driver end aligned for fitting into that anchor with the suture shown threaded through a longitudinal opening in that driver.

The tool 10 is shown in profile sectional view in FIG. 2, and in FIG. 4, a section of the anchor is shown exploded away from the hexagonal end 19 of the driver and shows a suture retaining disc 25 positioned therebetween. In FIG. 2, the two tool components, the anchor 11 and driver 12, are shown in longitudinal sectional view. The anchor and driver are separable, as will be explained in detail later herein with respect to FIGS. 4, 5A, 5B and 5C, but are operated together, the driver turning the anchor into a bone mass until they are separated, as set out above. At that separation the anchor will be seated a desired distance in the bone mass and a single or double strand of suture material will extend therefrom and out of the bone mass for securing a ligament thereto.

Figure 3:
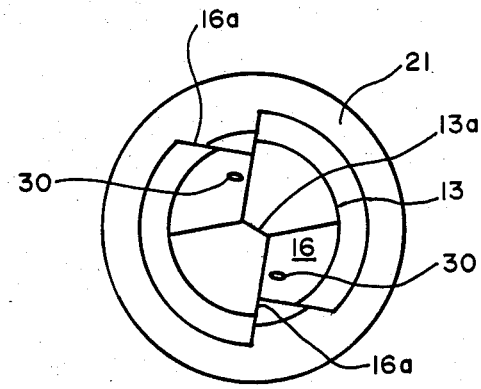
FIG. 3, is an end view of the fluted drill portion of the anchor taken along the line 3—3 of FIG. 1.

To turn the anchor 11 into a point on a bone mass, the anchor preferably includes a double fluted drill that is formed on one end thereof that consists of flutes 16 cut into opposite surfaces thereof that extend therealong and intersect a first flight 15 of threads 14 that are formed on the opposite or distal anchor end from the drill pointed end 13a. Threads 14 are made up of flights 15 that each preferably have a side or face that slopes rearwardly with respect to the drill pointed end 13a, at approximately a thirty degree (30°) angle to the vertical, the other side or face of each thread preferably formed at approximately a twelve degree (12°) angle to the vertical. The thread slope facilitates a first flight of threads engaging and turning into the hole bored in the bone mass. The threads 13 provide that with anchor 11 turning each thread flight 15, in turn, will engage and turn into the bore hole, the anchor thereby traveling into that bone mass to a desired depth, as will be explained with respect to a discussion of FIGS. 5A, 5B and 5C. The slope of each face of each thread 15 as to facilitate its turning into the bore hole, but resist its being turned out thereof, to lock thereby that anchor in the bone mass. As shown in FIG. 3, and as will be discussed in detail later herein, drill 13 includes two flutes 16 that are cut as opposite faces of the anchor drill end, each flute to have essentially a wide V shape with one of the surfaces 16a of the V being the cutting surface, and each flute is tapered outwardly from drill point 13a to and partially into the first flights 15 of thread 14. Additionally, as will be discussed in detail later herein, each flute is cut into anchor 11 to a depth so as to intersect a longitudinal hole formed in the anchor, as shown at 30 in FIGS. 1 and 3.

Shown in the sectional view of FIG. 2 the driver 12 includes, as an anchor engaging end for fitting into to turn anchor 11, a hexagonal sided end 19 that is formed to closely fit within and to contact in splined engagement the sides of a hexagonal faced area 18 that is formed in a longitudinal hole that is formed into the anchor adjacent to the anchor threads 14. So arranged, the respective sides of the driver end 19 contact the faces 18 of the longitudinal hole in anchor 11 to provide a splining of that anchor onto the driver, for transmitting torque therebetween, whereby, turning of the driver turns the anchor also. The driver 12 from the hexagonal end 19 is stepped outwardly into a collar 20 that has a diameter that is approximately that of the fluted drill 13 to follow the anchor into the hole bored in a bone mass. Distal from the hexagonal end 19 and collar 20, the driver is further stepped outwardly at a normal or right angle to form a shoulder 21 that is one end of body 17. The driver 12 is bored longitudinally from end to end, forming a first section 22 through the driver hexagonal end 19 and collar 20 that is of a diameter to just accommodate double strands of sutures 24 threaded therethrough. Opposite to shoulder 21, the first section 22 of the longitudinal hole is expanded into a second or larger cavity 23 wherein is shown folded the double strand sutures 24.

The double strand of sutures 24 that is threaded through the first section 22 is fixed within a longitudinal hole in the anchor 11. To fix the suture 24 in the anchor 11, shown best in FIG. 4, a disc 25 is provided that is centrally drilled at 26 so as to accommodate the suture 24 fitted therethrough. After such passage, the suture is knotted at 24a across the hole 26, to prohibit its withdrawal from the disc. Shown in FIG. 2 and in the exploded sectional view of FIg. 4, the anchor 11 is drilled longitudinally partially therethrough from an open anchor end adjacent to threads 14 to an apex 28 within the anchor. Therefrom, the longitudinal hole narrows to a section of lesser diameter 27 and the first section 18 of the longitudinal hole adjacent the anchor end is shown as being sided to have a hexagonal face, terminates in the apex 28. Shown in the expanded exploded view of FIG. 4, the disc 25 is aligned to be installed in that anchor longitudinal hole. The disc is champered along the outer circumference 29 thereof from a greater diameter at edge 29a to a lesser diameter at edge 29b, and edge 29a is preferably formed to have a sharp corner to bind into the wall longitudinal section 27, as will be described herein below. The lesser diameter edge 29b is preferably angled or rounded to pass freely into longitudinal hole second section 27.

Shown in FIG. 4, the double strand suture 24 is threaded through the disc opening 26 and knotted at 24a, such knot is preferably a single overhand knot, the knot to have a greater diameter or cross section than does the hole 26 so as to prohibit its passage back through that opening when a pulling force is applied to that suture. To install the disc 25 within the section 27 of the longitudinal hole in anchor 11, the disc is slid past the hexagonal sided opening 18 and into the lesser diameter section 27. The angled or rounded edge 29b is formed to slide freely therein, whereas the other greater diameter disc edge 29a is such that to effect its passage into the longitudinal hole, the disc must be forced or press fitted into that opening. The disc 25 is thereby forced into that longitudinal hole as illustrated in FIG. 2, the disc edge 29a binding into the longitudinal hole wall to prohibit its reverse passage therefrom. The disc 25 is preferably forced into the anchor longitudinal hole with an inserting tool. A preferred inserting tool, not shown, has an angle on the end to center a force applied thereby on the disc 25 center and distal therefrom includes a limiting shoulder to butt into the anchor end when the disc is properly inserted into section 27, before the knot 24a is squashed against apex 28. The angle on the inserting tool is selected for the purpose of forming the disc into a convex shape which will tend to lock tighter when force is applied to the sutures.

The anchor is constructed to have a minimum diameter whereby it will make only a small opening in a bone. Therefore, the disc 25 and anchor longitudinal hole wherein it is positioned must be of lesser but sufficient diameter such that the suture knot 24a will fit within that longitudinal hole proximate to apex 28. To accommodate knot 24a openings 30 are provided through the drill flutes 16 into that longitudinal hole that allow for some flecture of the longitudinal hole walls thereat so as to allow the disc edge 29a to travel therein, and allow the knot to partially extend therein. So arranged, the disc 25 edge 29a when the disc is inserted within the hole 27 tends to bite into the metal of the longitudinal hole wall prohibiting reverse passage of that disc such as could occur when a tensile force is applied to the suture 24. In practice, as set out in test data hereinbelow, it has been found that the suture will break before the disc will pull free from the longitudinal hole wall.

FIGS. 5A, 5B, and 5C show sequentially the operation of the anchor 11 being turned by the driver 12 to place that anchor in bone mass 31. Shown in FIG. 5A, the driver 17 end distal to its hexagonal end 19 is installed in a chuck 33. Chuck 33, it should be understood, is a conventional chuck of a hand or electric motor driven device for use in orthopedic procedures that involve drilling into a bone mass. Such chuck and device can include a hollow core that extends therethrough to accommodate the double stranded suture passed therethrough. It is, however, preferred, as is illustrated in FIG. 2, that the sutures are appropriately folded within the driver cavity 23. So arranged, the tool 10 with sutures therein can be provided to a doctor in a prepackaged sterile state for installation in the chuck 33.

In practice, as shown in FIGS. 5A, 5B, and 5C with the driver fitted into chuck 33, the surgeon can align or position the fluted drill pointed end 13a of the anchor 11 onto the bone mass whereat he desires to inset the anchor. Thereafter, by turning the chuck, the anchor drill 13 will bore a hole 32 into the bone mass 31, as illustrated in FIG. 5A. The drilling will continue until the first flight 15 of threads 14 engages the edge of hole 32. Thereat, the first thread flight 15, aided by its sloping configuration at its junction to one of the drill flutes, will tend to catch into the wall of that hole 32 and be drawn therein forming or trapping a thread into that hole wall. The following thread flights 15 will, thereafter, each turn easily in the thread in the hole 32 wall that is established by the first thread flight 15, as illustrated in FIG. 5B.

FIG. 5B shows the anchor 11 after it has been turned into the bone mass to a depth where the driver collar 20 has passed into that bored hole 32, and the driver shoulder 21 has butted into that portion of the bone mass surrounding the hole 32. Thereat, with continued turning of the driver 12, the anchor 11 will be turned further into the bone mass, while further entry of the driver 12 is stopped by shoulder 21 that is butting against that bone mass. The anchor 11, with continued turning, thereby slides off and moves out of its coupling engagement to the hexagonal driver end 19. When that separation occurs, the surgeon performing the procedure will feel the change in resistance to turning, and can, at that time, discontinue driver turning. The anchor 11 is thereby set at the desired depth within the bone mass, as illustrated in FIG. 5C, and thereafter the surgeon, by pulling the driver 12 out of the hole 32 will unfold the double strand of suture 24 from within the driver end 17, which suture is then available for connecting a ligament end or portion of a ligament to the point on the bone mass wherein the anchor 11 is set. After such connection, with time, the body processes will disolve the suture while the ligament is growing to that bone mass at that location. The suture anchor 11, as will remain permanently in the bone mass, so is preferably formed of a materal such as stainless steel, which can be left within the body.

In practice, it has been found that the tensile force necessary to dislodge the anchor 11 from the bone mass is much greater than the tensile force required to pull the knot 24a through disc hole 26 or break the suture. The way knot 24a is tied and suture strength is therefore critical to the use of tool 10 in the performance of a surgical procedure. In practice, a number of tests have been performed, as were set out hereinbelow, using a single strand of X/0.2(5.0 metric) eithibond brand polyester suture with the knot 24a, an overhand knot, tied by the inventor. The first column of the chart designs the test number. The tensile force applied to the suture is shown in pounds in a middle column, and the last chart column sets out what occured. From this data, it is apparent that the average or mean suture strength for this test was approximately 11.4 lbs.

| Test | lbs. | Affect |
|------|------|--------|
| 1A | 7 | Knot Pulled Out |
| 2A | 11 | Knot Pulled Out |
| 3A | 13 | Broke in Knot |
| 4A | 14.5 | Broke in Knot |

The above shows that the most likely point of failure of the invention was the suture connection to the anchor 11 at the knot 24a. To increase the pulling strength thereat, the inventor in a second set of tests set out hereinbelow, has applied a biocompatible cement to that knot that dried thereover to form a hard coating over that knot area. The test results show that with this coating, or a like hard coating, the pulling or tensile strength on the suture will be increased appreciably.

| Test | lbs. | Affect |
|---|---|---|
| 1B First Strand | 21 | Broke at Knot |
| 2B Second Strand | 18 | Broke at Knot |
| 3B First Strand | 20.5 | Broke at Knot |
| 4B Second Strand | 21 | Broke at Knot |

The present invention, as described above, resides in the suture anchor and a means for turning that anchor so as to seat it within a bone mass. A drill portion of the anchor has been shown herein to preferably consist of the two flutes, which two flute drill arrangement makes possible a use of a lessor diameter drill than would be possible with other drill shapes such as single or double twist or even a flat drill. It should be apparent, however, that other drill arrangements could be used within the scope of this disclosure. Also, while the individual flights 15 of threads 14 are shown sloping away from the drill end, it should be apparent that such slope would not be essential to the operation of the invention and that both faces of each thread flight could slope equally from the vertical. Additionally, while it has been illustrated that the longitudinal hole in anchor 11 at the second section 27 is preferably of a diameter to extend through the surfaces of drill flutes 16 at 30, it should be understood that the disc 25 can be securely and permanently seated in the anchor longitudinal hole even though that longitudinal hole does not break through the drill flutes. It should therefore be understood, that holes 30 can be dispensed within a practice of the invention.

The present disclosure has shown a preferred arrangement for coupling the driver to the anchor as, respectively, a hexagonal or six sided surface 19 formed in the driver end to fit within, in splined engagement, a portion or section 18 of a longitudinal cavity or hole having hexagonal or six faces. A hexagonal or six faces or sides is preferred as it provides sufficient faces to effect a splined engagement while still presenting a nearly round area within the anchor longitudinal hole to allow a free passage of the disc 25 therepast. It should, however, be obvious that a driver and opening in anchor end formed to have complementary surfaces but other than a hexagonal shape could be used within the scope of this disclosure. A limitation of use of such other shape, however, being that the selected shape would have to be such to allow passage of the disc 25 thereby or the disc would have to be appropriately shaped so as to allow for its passage therepast. As for example, if a three sided or triangular shaped driver end was so employed, the disc would have to be formed as a triangle to allow it to pass through that anchor end and, of course, the stepped down or second section 27 of the anchor longitudinal hole would have to be formed to accommodate that disc.

Also, while the invention is shown to preferably include folding the suture 24 upon itself within the driver cavity 23, as illustrated in FIG. 2, it should be understood that the suture could be allowed to extend beyond the driver fitting through a hollow barrel portion of a chuck and drill device wherein the driver is maintained within the scope of this disclosure.

While a preferred embodiment of the invention in a suture anchor and driver therefore has been shown and described herein, it should be apparent that this disclosure is made by way of example only and that variations are possible within the scope of this disclosure without departing from the subject matter coming within the scope of the following claims, which claims we regard as our invention.

We claim:

1. A suture anchor assembly comprising a cylindrically shaped anchor formed of a material suitable for implantation in a human body that includes both a drill means on one end thereof for boring, when turned, a hole in a bone mass, and a thread means that includes a plurality of thread flights formed in the anchor distal from said drill means end to turn into the bone mass following the drill means; means for securing a suture to said anchor to extend therefrom after said anchor is seated in the bone mass; and means for turning said anchor.

2. A suture anchor assembly as recited in claim 1, wherein the anchor drill means in a double fluted drill, the flutes cut into opposite anchor surfaces from a pointed end to intersect the screw means.

3. A suture anchor assembly as recited in claim 1, wherein the thread means includes a number of flights of threads where each of a face of each flight away from the anchor drill is sloped from the vertical at approximately a thirty degree (30°) angle.

4. A suture anchor assembly as recited in claim 1, wherein the means for securing a suture includes forming a longitudinal hole in said anchor end distal from the drill means to receive a suture retaining means therein; and a suture retaining means for maintaining a suture end secured thereto, and for fitting, in binding engagement, into said anchor longitudinal hole.

5. A suture anchor assembly as recited in claim 4, wherein the longitudinal hole is a hole bored centrally into said anchor to receive, as the suture retaining means, a disc that is holed centrally to receive a suture end threaded therethrough and knotted so as to prevent its withdrawal through that disc hole, which disc is for fitting into and binding within said anchor longitudinal hole.

6. A suture anchor assembly as recited in claim 5, wherein the knot tied in the suture end is coated with a biocompatible cement to provide a hardened coating thereover.

7. A suture anchor assembly as recited in claim 5, wherein the disc is formed to have a lesser diameter end to pass freely into the longitudinal hole, tapering therefrom to a greater diameter end to bind within the longitudinal hole.

8. A suture anchor assembly as recited in claim 4, wherein the longitudinal hole adjacent to the anchor end is faced with a number of flat sections therearound to receive an end of the means for turning the anchor that has a like number of flat sections formed around the outer circumference there to telescope into said anchor end to provide a spline coupling to said anchor.

9. A suture anchor assembly as recited in claim 8, wherein the anchor longitudinal hole is hexagonal faced with six (6) abutting edge to edge faces and the means for turning the anchor is likewise hexagonal sided with six (6) surfaces to telescope therein to provide a spline coupling therebetween.

10. A suture anchor assembly as recited in claim 8, wherein the means for turning said anchor is a driver having a cylindrical body and includes a central longitudinal passage therethrough, and said driver, distal from the hexagonal surface, is stepped outwardly into a cylindrical collar having the same diameter as does the anchor drill end to follow that anchor into a hole it bores into a bone mass.

11. A suture anchor assembly as recited in claim 10, wherein the driver distal from the hexagonal end and collar is stepped outwardly forming a shoulder that is at a right angle to said collar and is of a diamater to butt against the area of a bone mass around a hole bored by the anchor therein.

12. A suture anchor assembly as recited in claim 11, wherein the cylindrical driver end distal form the hexagonal end and collar has a diameter to fit within a conventional chuck.

13. A suture anchor assembly as recited in claim 12, wherein the central longitudinal passage therethrough is increased from a lesser to a greater diameter within the driver largest diameter portion to accommodate a length of suture folded therein.

14. A suture anchor assembly as recited in claim 4, wherein the longitudinal hole is formed in said anchor to intersect a point on the surface of the anchor drill means.

15. A suture anchor assembly as recited in claim 14, wherein the drill means is formed with two flutes the longitudinal hole intersecting and breaching points on each flute that are across from one another.

* * * * *

UNITED STATES PATENT AND TRADEMARK OFFICE
CERTIFICATE OF CORRECTION

PATENT NO. : 4,632,100
DATED : December 30, 1986
INVENTOR(S) : E. Marlowe Goble, et al.

It is certified that error appears in the above-indentified patent and that said Letters Patent is hereby corrected as shown below:

On the title page, item [75] inventors, should read--

E. Marlowe Goble and W. Karl Somers. ---.

Signed and Sealed this

Twenty-fourth Day of January, 1995

Attest:

BRUCE LEHMAN

Attesting Officer

Commissioner of Patents and Trademarks